United States Patent [19]

Saitoh et al.

[11] Patent Number: 4,915,940
[45] Date of Patent: Apr. 10, 1990

[54] FILM-FORMATION-TYPE ANTIFUNGAL PREPARATION

[75] Inventors: Izumi Saitoh, Hyogo; Kaori Ikeda; Yoshio Doi, both of Osaka; Shohei Egawa, Hyogo, all of Japan

[73] Assignee: Shionogi & Co., Ltd., Osaka, Japan

[21] Appl. No.: 271,304

[22] Filed: Nov. 15, 1988

[30] Foreign Application Priority Data

Dec. 8, 1987 [JP] Japan .................. 62-310480

[51] Int. Cl.⁴ .............. A61K 31/78; A61K 31/74; A01N 43/56; A01N 43/38
[52] U.S. Cl. .................. 424/81; 424/78; 424/409; 424/404
[58] Field of Search .............. 424/81, 78; 514/481, 514/781, 858

[56] References Cited

U.S. PATENT DOCUMENTS

| | | | |
|---|---|---|---|
| 3,989,815 | 11/1976 | Rajadhyaksha | 514/269 |
| 4,136,162 | 1/1979 | Fuchs et al. | 514/781 |

FOREIGN PATENT DOCUMENTS

| | | | |
|---|---|---|---|
| 1136045 | 11/1982 | Canada | 424/81 |
| 8159425 | 9/1983 | Japan | 514/781 |

Primary Examiner—Joseph L. Schofer
Assistant Examiner—Carmen Pili-Curtis
Attorney, Agent, or Firm—Wenderoth, Lind & Ponack

[57] ABSTRACT

Film-formation-type antifungal preparations for external application, consisting essentially of about 0.1% to about 1.5% of tolnaphtate, about 10% to about 20% of a dimethylaminoethyl methacrylate-methacrylic acid ester copolymer and 0.5% to about 10% of a medium chain fatty acid ester in an alcoholic solvent but containing practically no water.

5 Claims, 1 Drawing Sheet

FILM-FORMATION-TYPE ANTIFUNGAL PREPARATION

BACKGROUND OF THE INVENTION

1. Field of Invention

The present invention relates to preparations for topical application which contain tolnaphtate (hereinafter abbreviated as TOL) known as an antifungal agent. More specifically the Preparations of this invention are so designed as to form a flexible, strong, transparent film on the skin and gradually release TOL therefrom.

2. Prior Art

So far, tinctures, creams, gels, or the like preparations have been used for the topical treatment of mycosis.

TOL bas a potent action against fungi, especially against Trychophytons and therefore, it has long been used for the treatment of tinea pedis. However. in many cases, mycosis as represented by athlete's foot primarily occurs at moist Parts of the body. So, when an ointment or a gel preparation is applied to the affected part, it makes the affected part even more moist, thereby giving a strange feeling or staining clothing. These are shortcomings in using ointments or gel preparations. A tincture has such shortcomings as to take longer time to dry on the parts of the body to which it is applied. Furthermore it has been another shortcoming that conventional TOL-preparations result in TOL becoming crystallized in storage or when applied because of its property of being hardly soluble in most solvents.

SUMMARY OF THE INVENTION

The present invention provides film-formation-type anti-fungal preparations for topical application, consisting essentially of about 0.1% to about 1.5% of tolnaphtate, about 10% to about 20% of a dimethylaminoethyl methacrylate-methacrylic acid ester copolymer (hereinafter abbreviated as DMMA-MA), and 0.5% to about 10% of a medium chain fatty acid ester in an alcoholic solvent but containing practically no water.

BRIEF DESCRIPTION OF THE DRAWING

The ordinate shows TOL amount in the skin, while the abscissa shows time. The remaining amounts of TOL in the skin are shown by the mark "●" for the control and by the mark "○" for the Example 1 preparation disclosed below.

DESCRIPTION OF THE PREFERRED EMBODIMENT

Problems to be Solved

Figure 1:
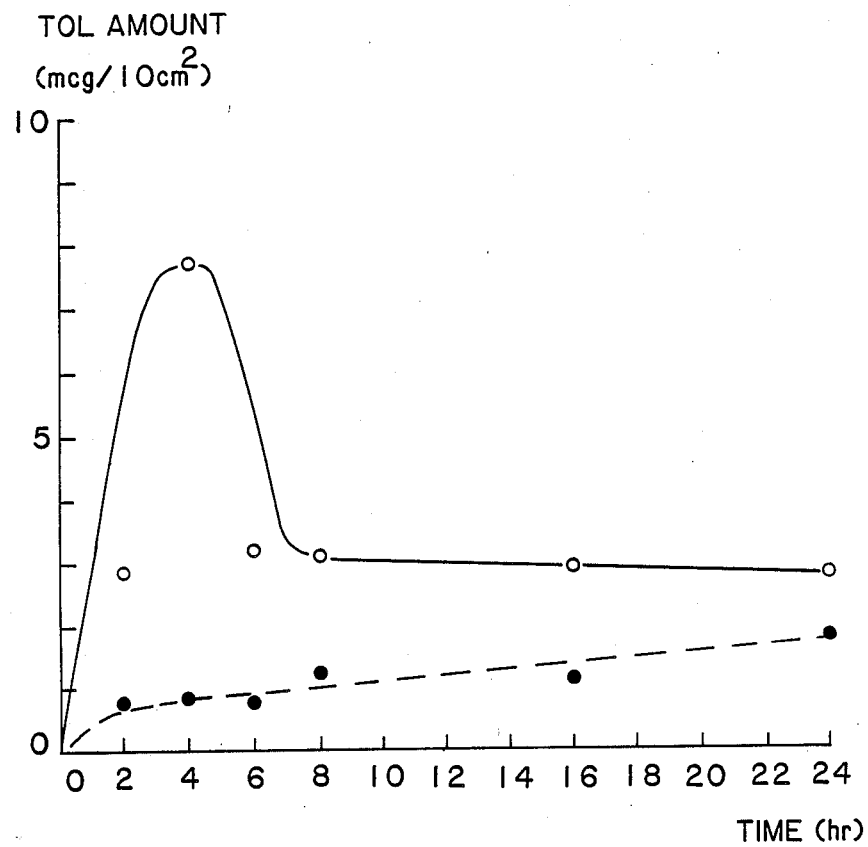

In view of the Problem above the present inventors tried to find such base ingredients as to prevent TOL from crystallization in storage or even after application, and as to enhance transdermal absorbability of TOL and, consequently, they have completed the present invention. The preparations of this invention enhance and sustain the action of TOL and, therefore, they are expected to give an excellent efficacy in a once-a-day application.

The preparations of this invention are capable of forming a flexible strong film on the skin when applied and of keeping the drug effect for a long period of time. Proportions used in this invention are shown as percentage by weight (w/w %) of certain additive to the total weight of the whole preparation.

Means to Solve the Problem

This invention can be achieved by dissolving about 0.1%— about 1.5% of TOL, about 10%—about 20% of DMMA-MA, and 0.5% —about 10% of a medium chain fatty acid ester in an alcoholic solvent. If necessary, about 0.1% —about 2.5% of a thickening agent and/or a plasticizer may be further added.

lOL used in this invention is a potent antifungal agent and very popular as cream- or gel-preparations. Eudragit ® E100 may be a good representative for DMMA-MA.

The medium chain fatty acid ester includes glyceryl monocaprate (GMC). tetraglyceryl monocaprate (TGMC), propyleneglycol dicaprate (PGDC), tetraglyceryl hexacaprate (TGHC), and the like. TGMC is especially preferred.

The aqueous alcohol used in this invention means such a dry lower alkanol as to contain substantially no water. Lower alkanol includes ethanol, propanol, isopropanol, and the like.

Thickening agents including cellulose derivatives such as ethyl cellulose (EC), hydroxypropyl cellulose (HPC), hydroxypropylmethyl cellulose (HPMC), and the like are preferably used. Plasticizers including propylene glycol (PG), polyethylene glycol (PEG), and the like are preferably used.

The tinea pedis preparations of this invention are remarkably improved in enhancing the transdermal absorbability of TOL and in making drug effectiveness last for a long time as compared with conventional preparations, creams, gels, tinctures or the like. So, it can be expected that once-a-day application of the preparation is enough to attain good efficacy. The present invention is explained in more detail in the following Examples and Experiments, which are not intended to limit the scope of the invention.

EXAMPLE 1

Isopropanol (76g) and 5g of TGMC were put in a closed type vessel equipped with a stirrer. DMMA-MA (15g; EUDRAGIT ® E100) and 3g of EC were gradually added thereto to give a clear solution, to which 1g of TOL was dissolved with stirring to make the objective preparation (100 g) of this invention.

EXAMPLES 2 –4

In substantially the same manner as in Example 1, the following instant preparations for tinea pedis were obtained.

TABLE 1

| | Example | | | |
| Components | 2 (%) | 3 (%) | 4 (%) | Control (%) |
| --- | --- | --- | --- | --- |
| TOL | 1 | 1 | 1 | 1 |
| DMMA-MA | 15 | 15 | 15 | 15 |
| GMC | 5 | | | |
| TGMC | | 5 | | |
| TGHC | | | 5 | |
| PG | | | | 3 |
| Ethanol | | 79 | 79 | 81 |
| Isopropanol | 79 | | | |

EXPERIMENT 1

The precipitation of crystals was examined to study shelf life stability on each of the following preparations. The e in solution and the presence of crystals were examined by observation with the eye or under a microscope.

Preparations Examined

Preparations manufactured in Examples 1 to 4
Control: Control preparation shown in Table 1

TABLE 2

| Preparation | Stored at 5° C. in tightly closed container | | | | | |
|---|---|---|---|---|---|---|
| | Initial | After 1 Week | After 2 Weeks | After 1 Month | After 2 Months | After 3 Months |
| 1 | — | — | — | — | — | — |
| 2 | — | — | — | — | — | O |
| 3 | — | — | — | — | — | — |
| 4 | — | — | — | — | — | — |
| Control | — | — | O | | | |

(Remarks)
—: No change in solution & no formation of crystals were observed.
O: Change in solution & formation of crystals were observed.

EXPERIMENT 2

The in vivo transdermal absorption study shown in the following experiments was carried out, basically according to the undermentioned method:

Test Method

1. Male Wister rats (9 weeks of age, n5-8) anesthetised by urethane have their abdominal hair removed carefully with electric clippers and electric razor.
2. The rat is fixed on its back, and then an absorption chamber (application area: 10 $cm^2$) is fixed on the surface of the hairless abdomen with an instant adhesive.
3. A pre-fixed dose of a test material (2 mg as TOL per rat) is placed into the chamber.
4. After a certain period of time, the coating film formed on the skin in the chamber is removed off with distilled water and collected into a suitable vessel.
5. The chamber is removed and the application area of the skin is cut off.
6. The sample in item 4 and the piece of the skin in Item 5 are employed for the TOL content measurement by HPLC.

Along the test method mentioned above, a comparative study for transdermal absorption of TOL was carried out on some instant preparations and a commercially available one. TOL amount in the skin 4 hours after application is as follows.

Result

TABLE 3

| Preparation | TOL Amount in the skin (mcg/10 $cm^2$) |
|---|---|
| Example 1 | 9.04 ± 2.50 |
| Example 2 | 3.97 ± 1.08 |

TABLE 3-continued

| Preparation | TOL Amount in the skin (mcg/10 $cm^2$) |
|---|---|
| Example 3 | 8.84 ± 2.85 |
| Example 4 | 6.21 |
| Commercially Available | 0.54 ± 0.06 |

Remarks

Commercially Available: Pasca® Gel (by Shionogi & Co., Ltd., containing 1% of TOL)

The instant preparations of this invention exhibit much her transdermal absorbabilities than the gel preparation commercially available one) which has generally been believed to exhibit: a high absorbability.

EXPERIMENT 3

TOL amounts in the skin were measured at several points of time for the preparation of Example 1 and a commercially available Preparation (1% Pasca® Gel: made by Shionogi & Co., Ltd.), to evaluate substantiality of TOL.

Result

The result is shown in the drawing. As compared with the control the preparations of this invention were remarkably improved in the transdermal absorbability of TOL and, additionally, they are capable of keeping high TOL concentrations in the skin for a long period of time. Consequently, the preparation of this invention exhibits a much larger area under the curve (AUC), the fact of which demonstrates a high bioavailability of TOL.

From those results, it is expected that the tinea pedis preparations of this invention will give an excellent efficacy in the treatment at only a once-a-day application.

What is claimed is:

1. A film-formation-antifungal preparation consisting essentially of about 0.1% to about 1.5% of tolnapbtate. about 10% to about 20% of a dimethylaminoethyl methacrylate-methacrylic acid ester copolymer, and 0.5% to about 10% of a medium chain fatty acid ester in an alcoholic solvent but containing practically no water.
2. The film-formation-antifungal preparation claimed in claim 1, wherein said medium chain fatty acid ester is tetraglyceryl monocaprate.
3. The film-formation-antifungal preparation claimed in claim 1, further containing about 0.1% to about 5% of a thickening agent.
4. The film-formation-antifungal preparation claimed in claim 1, wherein said alcoholic solvent is ethanol or isopropanol.
5. The film-formation-antifungal preparation claimed in claim 3, wherein said thickening agent is cthyl cellulose, hydroxypropyl cellulose, or hydroxypropylmethyl cellulose.

* * * * *